United States Patent [19]
Brune et al.

[11] Patent Number: 6,099,482
[45] Date of Patent: Aug. 8, 2000

[54] INGESTIBLE ANIMAL TEMPERATURE SENSOR

[75] Inventors: Scott A. Brune, Leo; Matthew R. Williams, Fort Wayne, both of Ind.

[73] Assignee: Innotek Pet Products, Inc., Garrett, Ind.

[21] Appl. No.: 09/210,175

[22] Filed: Dec. 11, 1998

Related U.S. Application Data

[63] Continuation-in-part of application No. 08/918,607, Aug. 22, 1997, Pat. No. 5,984,875.

[51] Int. Cl.[7] .................................................. A61B 5/00
[52] U.S. Cl. ........................................... 600/549; 119/174
[58] Field of Search .................. 600/549, 551, 600/591; 119/174

[56] References Cited

U.S. PATENT DOCUMENTS

| | | |
|---|---|---|
| D. 321,069 | 10/1991 | Stoddard, III . |
| 3,144,017 | 8/1964 | Muth . |
| 3,216,411 | 11/1965 | Watanuki et al. . |
| 3,229,684 | 1/1966 | Nagumo et al. . |
| 3,340,866 | 9/1967 | Noller . |
| 3,841,756 | 10/1974 | Grochowicz ............................. 356/72 |
| 3,893,111 | 7/1975 | Cotter . |
| 3,934,584 | 1/1976 | Corio ..................................... 128/223 |
| 3,948,249 | 4/1976 | Ambrosini .............................. 128/2 H |
| 4,165,033 | 8/1979 | Nielsen et al. ......................... 235/439 |
| 4,206,766 | 6/1980 | Bielka et al. .......................... 128/738 |
| 4,247,758 | 1/1981 | Rodrian ............................. 235/92 MS |
| 4,262,632 | 4/1981 | Hanton . |
| 4,305,402 | 12/1981 | Katims .................................. 128/741 |
| 4,399,821 | 8/1983 | Bowers . |
| 4,411,274 | 10/1983 | Wright .................................. 128/738 |
| 4,471,354 | 9/1984 | Smith ................................ 340/870.17 |
| 4,493,290 | 1/1985 | Gibbard .............................. 119/51 R |
| 4,537,150 | 8/1985 | Bowers ................................ 119/14.17 |
| 4,750,490 | 6/1988 | Haw et al. ............................. 128/330 |
| 4,784,155 | 11/1988 | Mills .................................... 128/734 |

(List continued on next page.)

FOREIGN PATENT DOCUMENTS

| | | |
|---|---|---|
| 649212 | 5/1994 | Australia . |
| 0 299 557 | 1/1989 | European Pat. Off. . |
| 0 395 188 | 10/1990 | European Pat. Off. . |
| 0 549 081 | 6/1993 | European Pat. Off. . |
| 83 09322 | 12/1984 | France . |
| 833599 | 5/1983 | South Africa . |
| 2 165 723 | 4/1986 | United Kingdom . |
| WO 8901722 PCT/US91/ | 2/1989 | WIPO . |
| 00104 | 7/1991 | WIPO . |
| WO 9517809 | 6/1995 | WIPO . |
| WO 98/01025 | 1/1998 | WIPO ............................ A01K 11/00 |

OTHER PUBLICATIONS

"Summertime Heat and Its Effect Upon Dairy Herd Profitability"; T. H. White, Jr.; Apr. 1, 1986.

"Detecting Heat in Dairy Cows", R. E. Marcoot, et al.; Jun. 1992.

"Detecting Estrus in Dairy Cattle"; D.A. Colman; Oct., 1993.

"Injectable Electronic Identification"; Sidney L. Spahr; Oct., 1993.

*Primary Examiner*—Max Hindenburg
*Attorney, Agent, or Firm*—Taylor & Aust, P.C.

[57] ABSTRACT

A system and ingestible boluses for monitoring physiological parameters of animals. The boluses include circuitry for storing a selectable identification code, for sensing a physiological parameter, and for transmitting a data burst signal which includes information corresponding to the identification code and a sensed physiological parameter. In addition to the boluses, the system includes a receiver for receiving data burst signals transmitted from the boluses. According to one mode of operation, the bolus transmits data burst continuously at a preselected rate. The receiver can be coupled to a processor which can process data from the data burst signals.

19 Claims, 12 Drawing Sheets

U.S. PATENT DOCUMENTS

| | | | |
|---|---|---|---|
| 4,844,076 | 7/1989 | Lesho et al. . | |
| 4,854,328 | 8/1989 | Pollack | 128/736 |
| 4,865,044 | 9/1989 | Wallace | 128/736 |
| 4,895,165 | 1/1990 | Blair | 128/738 |
| 5,024,221 | 6/1991 | Morgan . | |
| 5,111,799 | 5/1992 | Senger et al. | 128/738 |
| 5,217,011 | 6/1993 | Bisch . | |
| 5,241,924 | 9/1993 | Lundin et al. | 119/51.02 |
| 5,415,181 | 5/1995 | Hogrefe et al. . | |
| 5,481,262 | 1/1996 | Urbas | 340/870.17 |
| 5,482,008 | 1/1996 | Stafford et al. . | |
| 5,499,626 | 3/1996 | Wilham et al. . | |
| 5,542,431 | 8/1996 | Starzl | 128/738 |
| 5,653,239 | 8/1997 | Pompei | 128/664 |
| 5,697,384 | 12/1997 | Miyawaki | 128/899 |

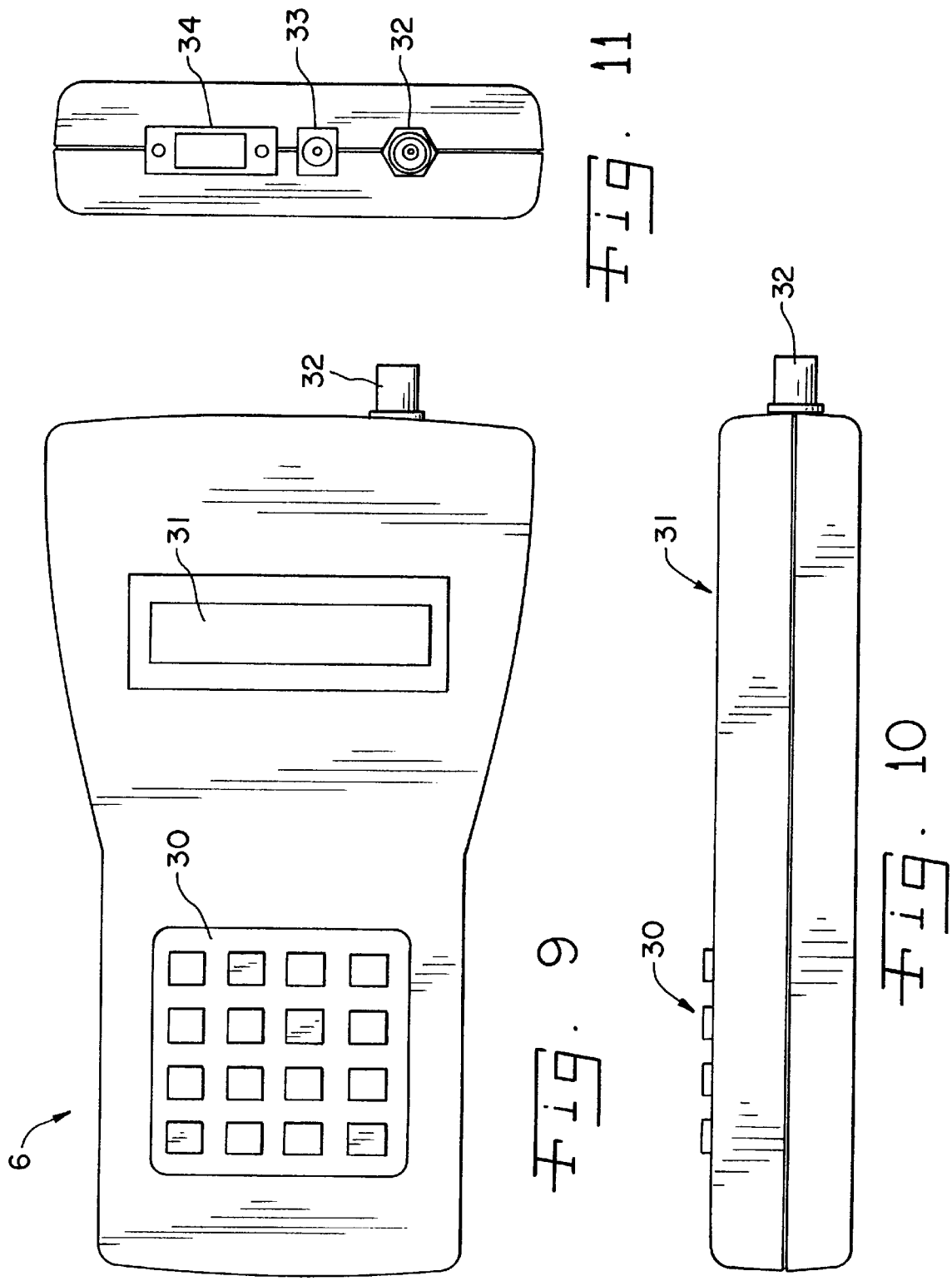

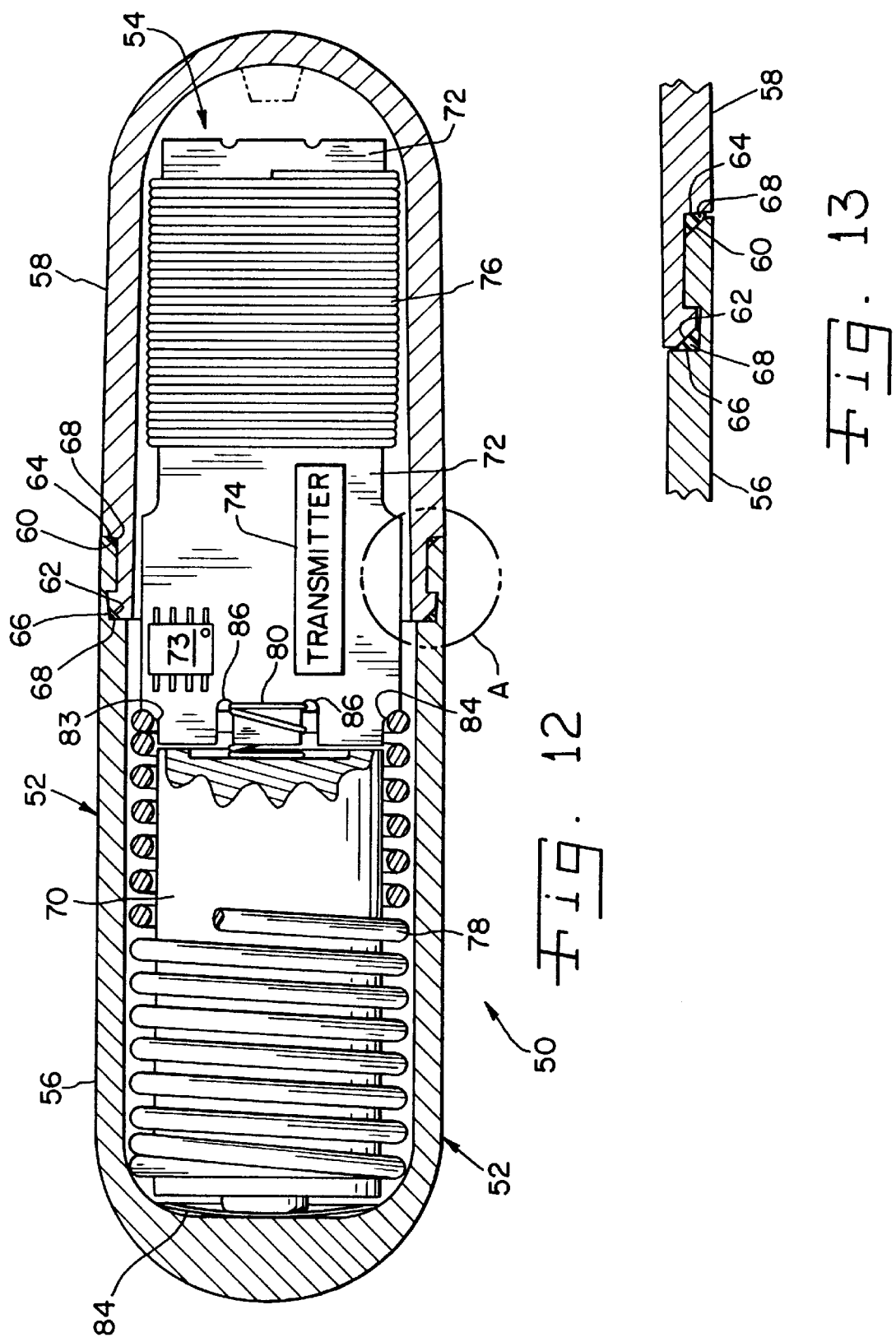

INGESTIBLE ANIMAL TEMPERATURE SENSOR

This is a continuation-in-part of U.S. patent application Ser. No. 08/918,607 filed Aug. 22, 1997, now U.S. Pat. No. 5,984,875.

TECHNICAL FIELD

The present invention relates to a system and apparatus for monitoring the core temperature of ruminant animals. More particularly, the present invention relates to an ingestible bolus which, when swallowed by a ruminant animal, can be used to sense and transmit information, including the core temperature of the ruminant animal.

BACKGROUND ART

There are several reasons for monitoring the core temperature of ruminant animals, including determination of sickness or disease and for breeding purposes. Temperature changes of one degree Fahrenheit or less can signal a change in the physiological state of a ruminant animal. Early detection of such physiological changes would allow ranchers, feed lot operators, dairymen and others to take necessary action to prevent the spread of sickness and disease, to treat a sick or diseased animal in a timely manner, or to monitor breeding conditions.

The problem of monitoring the temperature of individual animals in a herd becomes complicated, especially when the herd is allowed to roam over a wide area. In order to monitor the temperature of individual animals in a herd, it is necessary to correlate temperature measurements with specific animals.

Several attempts have been made to provide systems for remotely monitoring the temperature of animals.

U.S. Pat. No. 5,482,008 to Stafford et al. discloses an electronic animal identification system which includes a bolus that is administrated into the rumen or reticulum of a ruminant animal. The bolus includes an electronic identification device and an optional temperature sensor. In operation, boluses transmit the identification and temperature data only in response to an interrogation unit outside the animal.

U.S. Pat. No. 4,399,821 to Bowers discloses a free moving animal physiological monitoring and identification system which includes an implanted device which may be swallowed and located in the stomach of an animal. The system utilizes a parameter interrogator to obtain temperature data from the implant.

U.S. Pat. No. 4,262,632 to Hanton et al. discloses an electric livestock identification system which includes a transmitter capsule which can be placed in the reticulum of an animal. An interrogator-receiver unit is used to power the capsule and receive identification data.

U.S. Pat. No. 3,893,111 to Cotter discloses a system for remote monitoring of animal temperature which includes a capsule that contains a variable length antenna which changes in length according to temperature. The capsule is embedded into an animal and activated by a remote interrogation unit.

Collectively, prior art devices which are designed to remotely monitor animals such as cows suffer from a number of similar problems which render the systems in which they are used less than satisfactory both from manufacturing and performance stand points.

For example, the data transmission ranges for known prior art devices are limited to six meters or less. This limitation renders such devices and their related systems unacceptable for monitoring animals which are allowed to roam freely. Although one solution for this problem is the use of a network of receivers with overlapping ranges, the cost for such a system can be prohibitive. Moreover, there are failure and maintenance problems which increase with increasing numbers of receivers, as well as potential power supply problems.

Identification codes which are presently used in animal monitoring devices are set during manufacturing, so that a user of such devices is required to order a series of sequentially coded devices. Care has to be taken to keep track of the identification code of each device. Moreover, when herds of animals are mixed together or within the proximity of a common receiver, it is possible for two or more devices to transmit similar identification codes.

Battery life of implanted monitors is severely limited in prior art systems. Although the solution for extending battery life has been to limit data transmission to times when the monitors are interrogated, the actual battery life of such monitors is far less than the expected life or service life of the animals. Accordingly, once the batteries in an implanted device fail, an additional implanted device must be incorporated into the animal. Adding additional objects into the rumen or reticulum of a ruminant animal may not be desirable.

Another disadvantage with interrogating the implanted devices is that the need for interrogation limits the range at which the devices can be used. Although this is not a problem since the actual useful ranges of known devices are inherently limited, the requirement of interrogation does enforce the useful range limitations on systems using the prior art monitors.

Prior art devices which include temperature sensors, involve a trade-off between temperature accuracy and the cost of circuit tuning elements, thereby requiring that each implanted device be individually tuned and calibrated. Such individual tuning and calibration adds addition expense to manufacturing costs which are compounded by the circuit tuning elements. Prior art devices such as U.S. Pat. No. 3,893,111 to Cotter which use mercury containing temperature sensors can be hazardous if they malfunction and leak mercury.

Prior art systems in general are susceptible to magnetic and electrical interference to the point that they will display incorrect data or become desensitized and fail to operate at all.

Magnetic interference can result from implants being too close in proximity to magnets. In this regard, it is common practice to insert magnets which permanently reside in the reticulum of animals to attract and collect magnetic objects so that such objects do not pass through the gastrointestinal tract of the animal and cause health problems. Implanted monitors or sensors can become lodged in close proximity to such magnets and thus be adversely affected by their magnetic fields.

The circuitry in prior art implanted devices may also be subject to electrical interference which effects detuning of the resonant frequency of the devices' antennas. Such electrical interference can result if the devices are in close proximity to magnets or any other conductive materials.

The present invention provides an ingestible temperature sensor that has a number of advantages over prior art devices.

SUMMARY OF THE INVENTION

Generally, the present invention provides a system for monitoring physiological conditions, such as the temperature of individual animals in a herd or group of animals.

The present invention also provides a system for monitoring the temperature of individual animals in a herd or group of animals which system includes a ingestible bolus that transmits unique identification codes together with sensed physiological parameters such as temperature. The transmitted data is received by a receiver unit which is capable of collecting, analyzing and correlating data. The receiver unit can be a remote, hand-held receiver which can be used in the field to interrogate implanted boluses and cause them to transmit a data signal on demand which data signal is received by the receiver. Otherwise the boluses can transmit data bursts in random periodic cycles.

The present invention provides a highly accurate monitoring system which is capable of monitoring physiological conditions of the animals over large distances, so that the animals are allowed to roam freely on a farm, dairy, range, or similar facility.

The boluses include circuitry which allows the identification codes for the monitors to be programmed in the field. In addition to being field programmable before implantation or ingestion, the boluses are also capable of being programmed within the rumen or reticulum of an animal. This allows the user to change identification codes if necessary, to turn the bolus off and on, and to change the frequency period of autonomous data transmission to allow for faster or slower data collection rates as desired.

According to one mode of operation, the bolus provide an autonomous periodic data transmission which allows constant 24 hour monitoring of the physiological conditions of animals with automatic data collection and analysis. The system can be used to analyze collected data and provide an alert signal which is set for any critical change in the status of an animal or group of animals at any time. The system can thus provide automatic determination of milk fever, heat stress, mastitis and other illnesses or diseases which require immediate attention in order to prevent loss of milk production resulting from stress. The boluses of the present invention are capable of continuous 24 hour operation for the useful life of an animal which is estimated to be three years or greater.

The system of the present invention incorporates an error detection and correction algorithm, which provides maximum immunity to electrical noise and interference for the radio frequency data transmission link.

The system of the present invention is more economical to produce prior systems, because it allows for high accuracy and resolution of physiological data measurements without the need for individual tuning or adjustment of the boluses. In addition, the invention utilizes transmission frequencies which allow for optimum performance without the need for FCC licensing.

The ballast which is used in the boluses to increase their density can include a magnetic material. This will eliminate the need for an additional magnet which may be implanted in the rumen or reticulum of an animal to collect metal objects. The boluses of the present invention are designed to operate properly when exposed to or in contact with magnets which may already be present in the reticulum of an animal.

BRIEF DESCRIPTION OF THE DRAWINGS

The present invention will be described hereafter with reference to the attached drawings which are given as nonlimiting examples only, in which:

FIG. 9 is a front view of a hand held receiver according to one embodiment of the present invention.

FIG. 10 is a side view of the hand held receiver of FIG. 9.

FIG. 11 is an end view of the hand held receiver of FIG. 9.

FIG. 12 is a sectional view of another embodiment of an ingestible bolus sensor of the present invention.

FIG. 13 is an enlarged, fragmentary view illustrating the sealed interconnection between the two bolus halves, taken at detail A in FIG. 12.

DETAILED DESCRIPTION OF THE INVENTION

Figure 1:
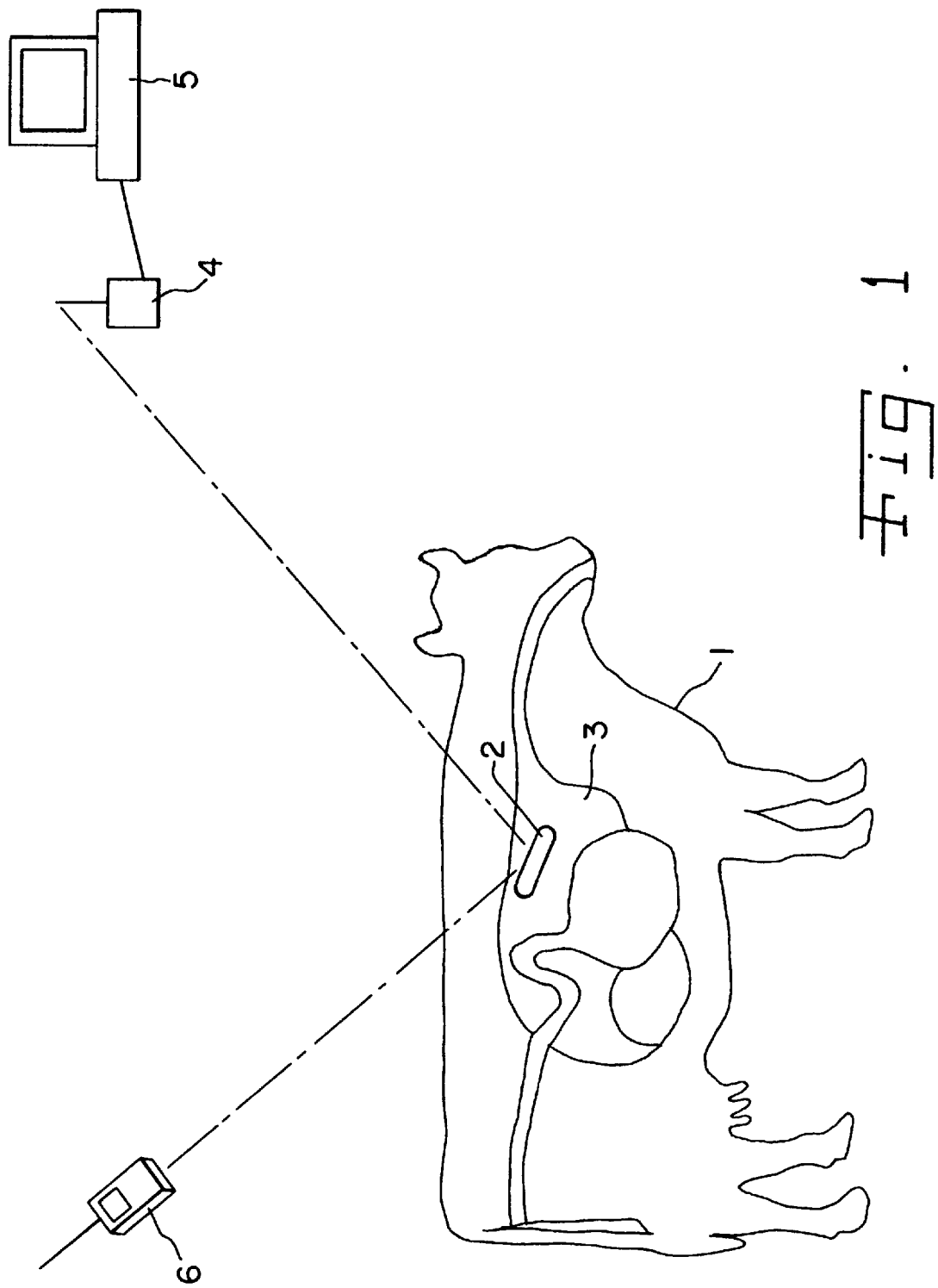
FIG. 1 illustrates a system in accordance with the present invention showing a cow with an ingestible sensor positioned in its reticulum.

The present invention is directed to a system and apparatus for monitoring the core temperature of ruminant animals. The system includes an ingestible bolus which, when swallowed by a ruminant animal, senses and transmits information, including the core temperature of the ruminant animal. The system further includes a receiver which receives the information transmitted from the ingestible boluses. The bolus has a suitable size and density which ensure that it is not regurgitated from the animal's rumen or reticulum. The bolus is capable of remaining in the animal's rumen or reticulum throughout the life of the animal.

In addition to having a particular size and density which ensure that the bolus will remain in the animal's rumen or reticulum, the exterior surface of the bolus is made from a suitable material which will withstand the environment of the animal's rumen or reticulum. Plastics are particularly useful as a material for the boluses, because plastics are inexpensive and can be easily molded.

The boluses include means for transmitting a signal. The transmitted signal comprises a data burst which can include an identification code for individual animals as well as temperature data. According to a preferred embodiment, the transmitted temperature data provides a signal that can produce a readout which is accurate to one-tenth of a degree Fahrenheit. Each bolus produces a transmission or data burst at a time interval which has a random factor. This randomness helps ensure that, when a large number of the boluses are used, for example in a large herd of cows, the likelihood of two boluses transmitting a signal or data burst simultaneously is very low.

The receiver is preferably coupled to a computer or other processor unit which can, upon receiving a signal transmitted from a bolus, display the identification number of the corresponding animal and/or the temperature sensed by the bolus. The computer or processor can also store the identification number and sensed temperature and, in addition to other functions, may produce any of a number of histories, correlations or calculated values such as temperature averages. The computer or processor may also include an audio or visual warning which is triggered when one or more sensed temperatures are above or below a set threshold.

In normal operation, the receiver and associated computer or processor are located in an area such as a house, barn or other building where transmitted information can be conveniently accessed and monitored. The boluses are designed to transmit data over a range of two hundred yards and more. This range is sufficient to allow animals who have ingested the bolus to roam or graze freely within an operable proximity to the receiver.

According to another embodiment, the receiver is provided as a hand held unit which includes a processor and display. The hand held receiver allows a user to inspect a herd or group of animals in the field. In this regard, the hand held unit can be provided with a circuit which interrogates the ingestible boluses to obtain information such as an animal's identification code and sensed core temperature on demand.

The ingestible bolus includes a sensor for sensing physiological parameters of an animal. According to one embodiment, a temperature sensor such as a highly accurate monolithic temperature sensor is used to sense the core temperature of an animal. Other physiological parameters can be sensed by incorporating sensors such as electrical pH sensors, and similar sensors that can be used monitor other chemical components that are susceptible to redox reactions, pressure sensors, and the like.

FIG. 1 illustrates a system in accordance with the present invention showing a cow 1 with an ingestible bolus 2 positioned in its rumen or reticulum. As shown in FIG. 1 the basic system of the present invention involves the use of an ingestible bolus 2 which is adapted to be internally implanted in a ruminant animal, such as a cow 1 for permanent residence in the animal's rumen or reticulum 3, and a receiving unit 4 which receives a transmitted signal from the ingestible bolus 2 and provides a read-out of transmitted data. The ingestible bolus 2 can be orally administered to an animal using a balling gun in a known manner.

The ingestible bolus 2 has a suitable size and density which ensure that it is not regurgitated from the cow's rumen or reticulum 3. The ranges of such parameters are known from the conventional use of cow magnets. Ideally, the bolus 2 will remain in the animal's rumen or reticulum 3 throughout the life of the animal, and can be recovered at the time the animal is slaughtered. The sensor and signal transmission circuit in the ingestible bolus 2 can be powered for three years or more by a battery.

The receiver 4 is ideally located in an area such as a house, barn or other building where transmitted information from the ingestible bolus 2 can be conveniently accessed and monitored. The signal transmitted from the ingestible bolus 2 comprises a data burst which includes an identification code and temperature data. As discussed below, the identification code can be field programmed into the ingestible bolus 2 so that a unique identification number can be assigned to a multiplicity of ingestible boluses, each of which can be administered to different animals. In this manner, each of a plurality of animals, e.g. cows in a herd, can be implanted with the ingestible boluses, and the temperature of each animal can be individually monitored.

In addition to displaying a read-out of the data transmitted from each ingestible bolus 2, the receiving unit 4 can be equipped with or linked to a computer or processor 5 which stores the identification code and sensed temperature. The computer or processor 5 could also be used to produce any of a number of histories, calculations, or correlations from the received data. The computer or processor 5 may also include or be coupled to an audio or visual warning which is triggered when one or more sensed temperatures are above or below a set threshold.

FIG. 1 also depicts a hand held receiver 6 which can be used to receive data burst signals from the ingestible boluses. The hand held receiver also includes a processor and circuitry to display information such as an animal's identification code and sensed core temperature. In addition, the processor can be used to correlate received data. According to another embodiment of the present invention, the hand held receiver 6 could be provided with circuitry to interrogate the ingestible bolus 2. This would allow a user to inspect a group of animals in a field environment and distinguish individual animals by their identification codes. Such integration circuitry could also be provided with receiver 4.

Figure 2:
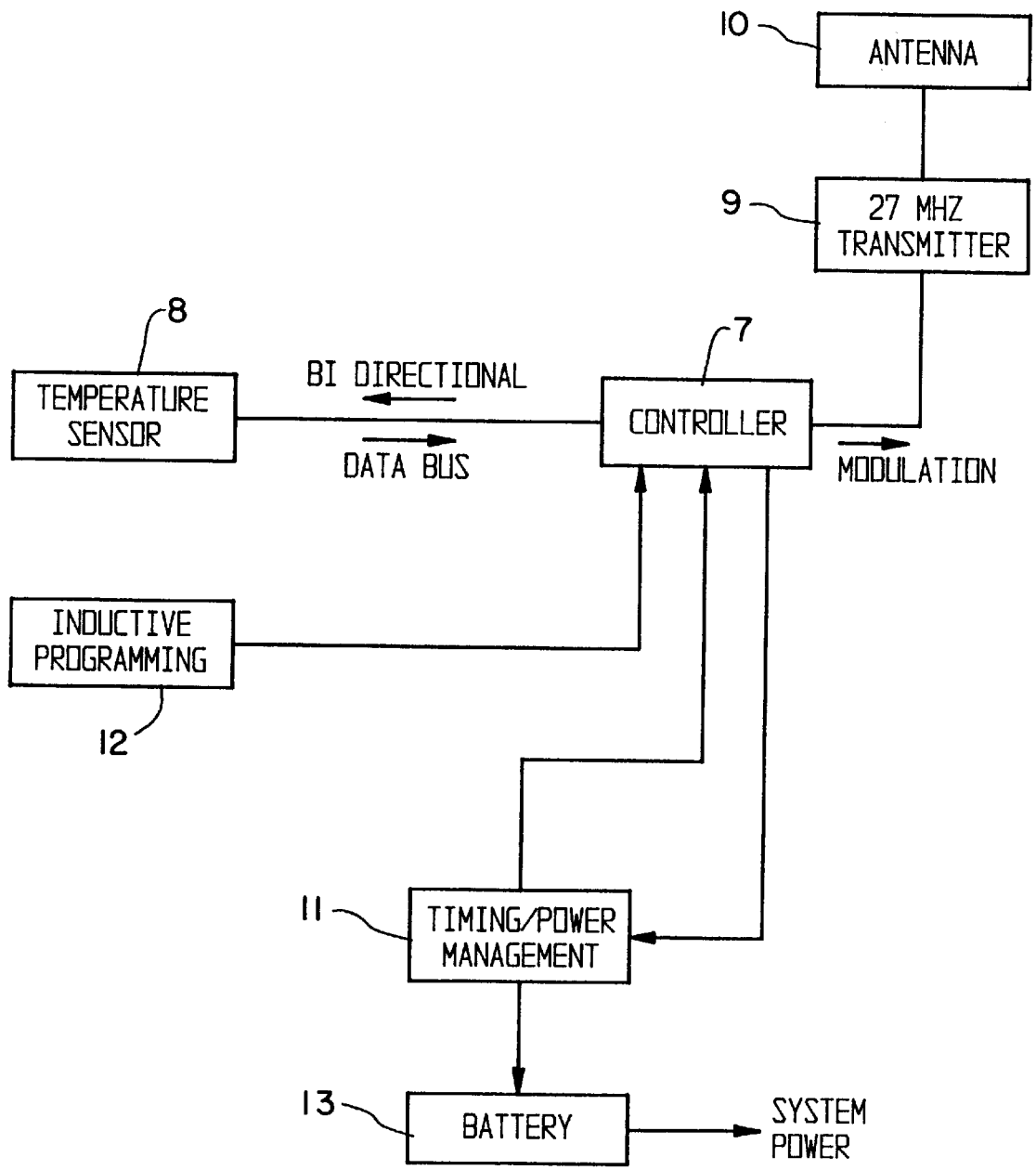
FIG. 2 is a block diagram which depicts the basic functioning of an ingestible sensor according to one embodiment of the present invention.

FIG. 2 is a block diagram which depicts the basic functioning of an ingestible bolus according to one embodiment of the present invention. As depicted in the block diagram of FIG. 2, controller 7 controls the operation of the ingestible sensor circuit via a bi-directional data bus. Controller 7 activates and receives signals from the temperature sensor 8, controls transmitter 9 which transmits a data burst via antenna 10, and controls timing/power management circuit 11. Controller 7 is externally programmed by inductive programming 12. For example, the controller 7 can be inductively programmed to set an identification code, the cycle period for data bursts, a calibration factor for the temperature sensor, etc.

The ingestible bolus is powered by a battery 13 and includes a timing/power management circuit 11 which conserves battery life by maintaining the bolus in a "sleeping" mode until data bursts cycles are triggered. The timing/power management circuit 11 turns the system power on, causing controller 7 to activate temperature sensor 8 and obtain therefrom a temperature signal. The controller 7 then encodes the temperature signal and an identification code with an error detection and correction algorithm and 0.feeds encoded data signal to transmitter 9 which transmits the encoded data signal as a data burst via antenna 10.

Figure 3A:
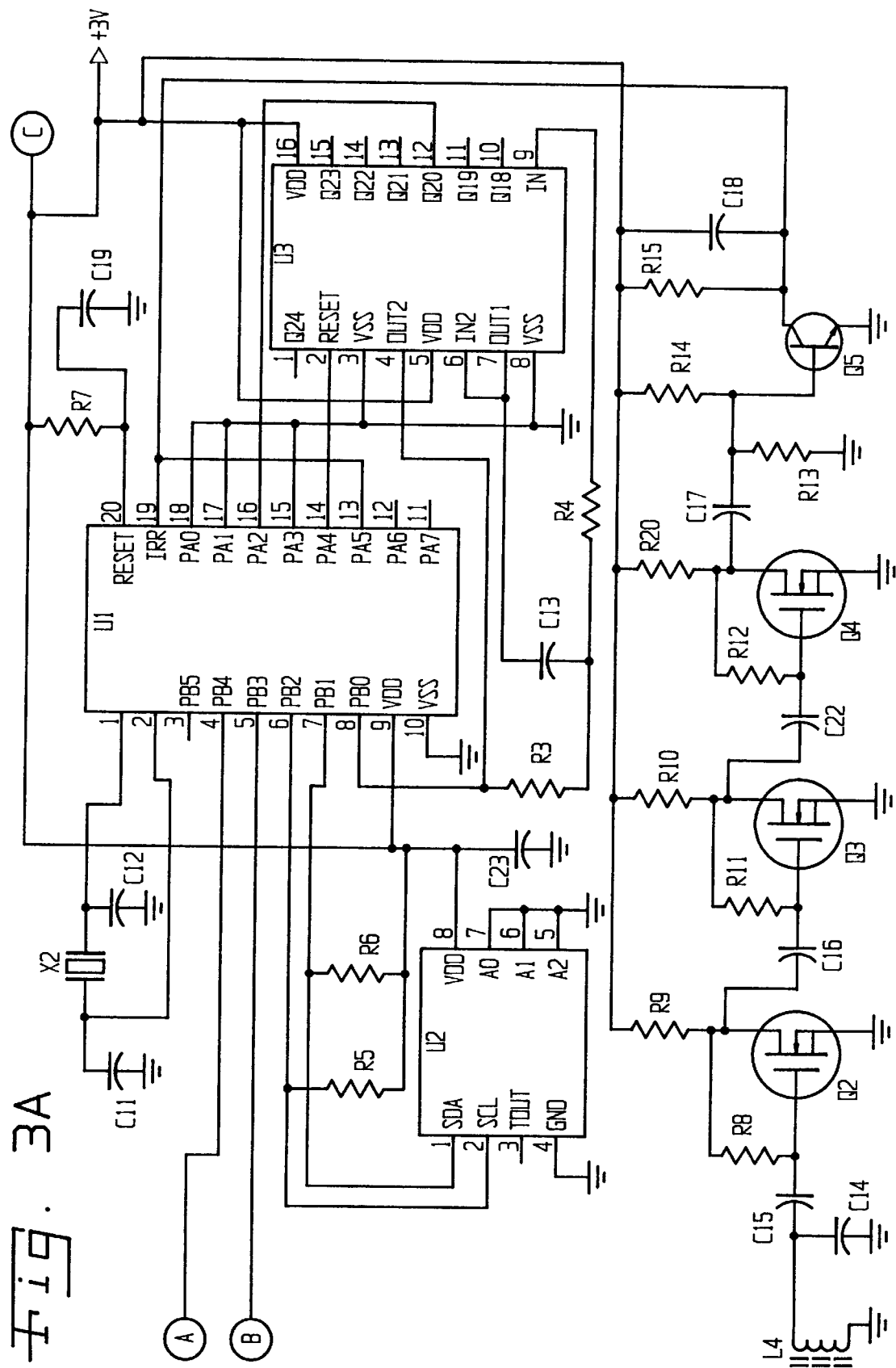
FIGS. 3A and 3B are a circuit diagram for an ingestible sensor according to one embodiment of the present invention.
Figure 3B:
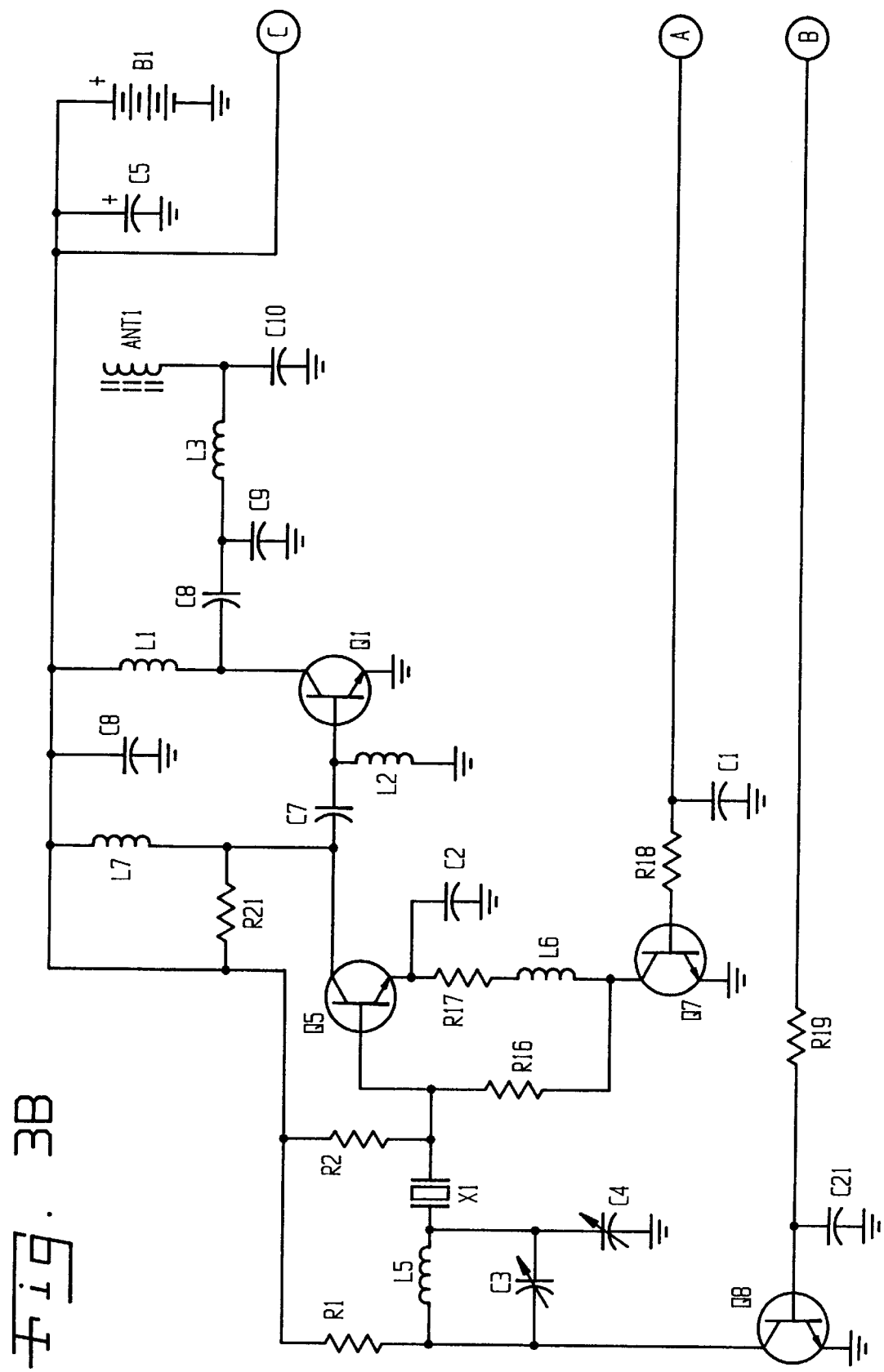

FIG. 3 (conjunctively 3A and 3B) is a circuit diagram for an ingestible bolus according to one embodiment of the present invention. Unless otherwise specified throughout the drawings, resistance is in ohms, capacitance is in microfarads and inductance is in microhenries. It is noted that the circuits depicted in FIGS. 3, 4, 8a and 8b, and the specific components thereof are exemplarily only of workable embodiments of the present invention. These circuits and the components thereof can be adapted for different operating parameters and conditions as desired.

The circuit depicted in FIG. 3 utilizes frequency shift keying (FSK) for signal modulation so that amplitude variations of radio frequency (RF) signal are not part of the information transfer. This allows for a Class C final RF amplifier which is more efficient than a Class A or B amplifier. In the circuit of FIG. 3 inductor L4 and capacitor C14 form a tuned resonant circuit at 10.7 $KH_2$ with the inductor picking up magnetically coupled external transmitted modulator 10 KHz signals. The modulation rate is 125 Hz. Field-effect transistors Q2, Q3, Q4 and transistor Q5 form a 10.7 KHz high gain very low power consumption amplifier cascade. The collector of Q5 is connected to the collector circuit voltage (Vcc) via the RC filter which includes resistor R15 and capacitor C18. The RC filter demodulates the 10.7 KHz signal and delivers an active low 125 Hz signal to an interrupt pin of the microprocessor (U1) (pin 19). This circuitry is used to interpret externally transmitted signals for control of all of the modes of the ingestible boluses.

The bolus has the following modes which can be externally (inductively) controlled: A POWER mode for turning the boluses on and off. A PROGRAMMING mode for selecting an identification (ID) code and autonomous transmission interval. A TEST mode in which the boluses transmits data bursts repeatedly for testing. A QUERY mode in which interrogation of the boluses results in the transmission of a data burst.

The modes of the bolus are controlled by an 8 bit microprocessor U1. The microprocessor U1 is normally in a power down low quiescent current condition until timer control chip U3 wakes the microprocessor U1 up. The clock rate of the timer control chip U3 is determined by the resistor capacitor combination of R3, R4 and C13 and is set for approximately 800 Hz. The timer control chip produces a clock with a rate of approximately 7.5 min. which is fed to pin 16 of microprocessor U1. Upon receipt of the positive transition of the clock, the microprocessor U1 "wakes up" and checks to determine what transmission rate has been programmed. If the 30 min. rate is selected, the microprocessor will increment an onboard counter and go back to sleep. This cycle will repeat until a count of four is reached, at which time microprocessor U1 will query the temperature sensor U2 for a temperature reading via a bidirectional serial data (U1, pin 7) and clock (U1 pin 6) lines. After a minimum time period of 200 msec, the temperature sensing IC sends a digital 13 bit temperature reading back to the microprocessor U1. The microprocessor U1 then combines this 13 bit temperature data with the stored identification code and uses an error detection and correction (EDAC) algorithm, e.g. a Hamming EDAC algorithm to precode the 32 bit data transmission word. If a 7.5 min cycle is chosen, the microprocessor U1 will implement the temperature query process on each clock cycle.

The microprocessor U1 than turns on the RF transmitter modulator by switching the base of transistor Q7 high, thereby turning on the 27.145 MHZ oscillator (formed by transistor Q6 and crystal X1) along with bias and tuning resistors, capacitors, and inductors L7, C22, R16, R17, L6, C4, and R2. The microprocessor U1 controls the frequency of the oscillator by switching transistor Q8 on and off. This switching inserts the frequency shifting network R1, L5 and C3 into the circuit, which pulls the resonant frequency of the crystal lower. Capacitor C4 controls the upper resonant frequency and capacitor C3 controls the lower resonant frequency. Frequency shift keying is accomplished by switching between the upper and lower frequencies.

The oscillator output is coupled via capacitor C7 to the input of amplifier Q1 thereby providing sufficient drive to turn on amplifier Q1. The output of amplifier Q1 is then matched to the coil antenna with a lowpass filter network which includes capacitors C8, C9 and C10 and inductor L3. The RF signal energy is then radiated to the receiver from the coil antenna ANT 1. The antenna coil is designed to be resonant with the dielectric loading of the reticulum or rumen environment taken into account.

Figure 4A:
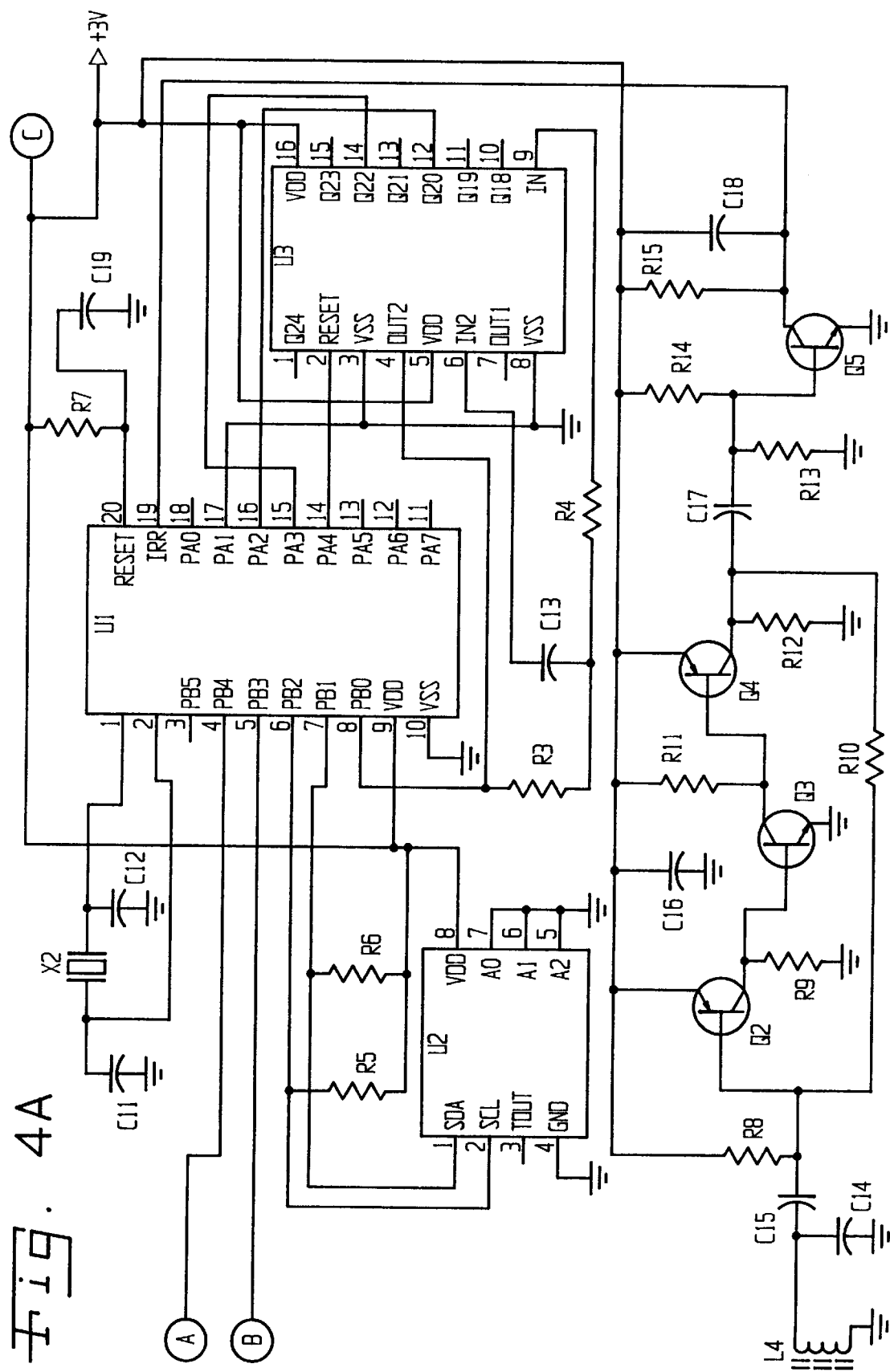
FIGS. 4A and 4B are a circuit diagram for an ingestible sensor according to another embodiment of the present invention.
Figure 4B:
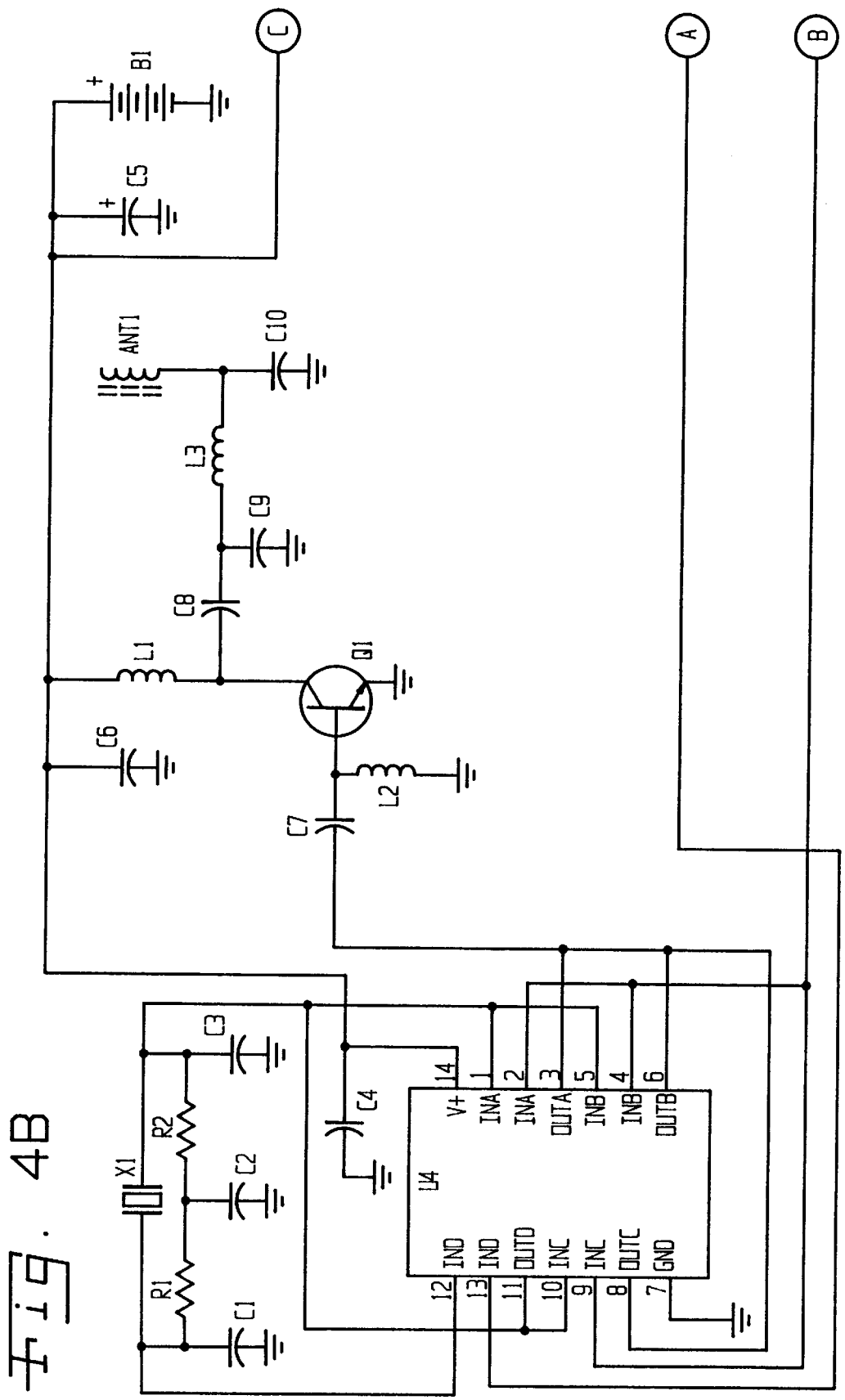

FIG. 4 (conjunctively 4A and 4B) is a circuit diagram for an ingestible bolus according to another embodiment of the present invention. The circuit depicted in FIG. 4 utilizes binary phase shift keying (BPSK) for signal modulation so that amplitude variations of radio frequency (RF) signal are not part of the information transfer. This allows for a Class C final RF amplifier which is more efficient than a Class A or B amplifier.

The circuit diagram of FIG. 4 is similar to the circuit diagram of FIG. 3 except that the frequency shift keying circuitry is replaced by an oscillator/BPSK modulator on a high speed CMOS quad exclusive OR integrated chip (IC) U4. One gate is used for a simple invertor oscillator formed by using 27.145 MHZ crystal X1 in the feedback path. This oscillator is turned on/off by the microprocessor U1 (pin 4). The remaining 3 gates in the IC U4 are paralleled together to get better output drive, and with the oscillator as one input the signal level of the microprocessor U1 (pin 5) is used to phase modulate the 27.145 MHZ signal between 0 and 180 degree phase shifts. The output of the modulator feeds the class C amplifier as discussed in reference to FIG. 3 above.

Figure 5:
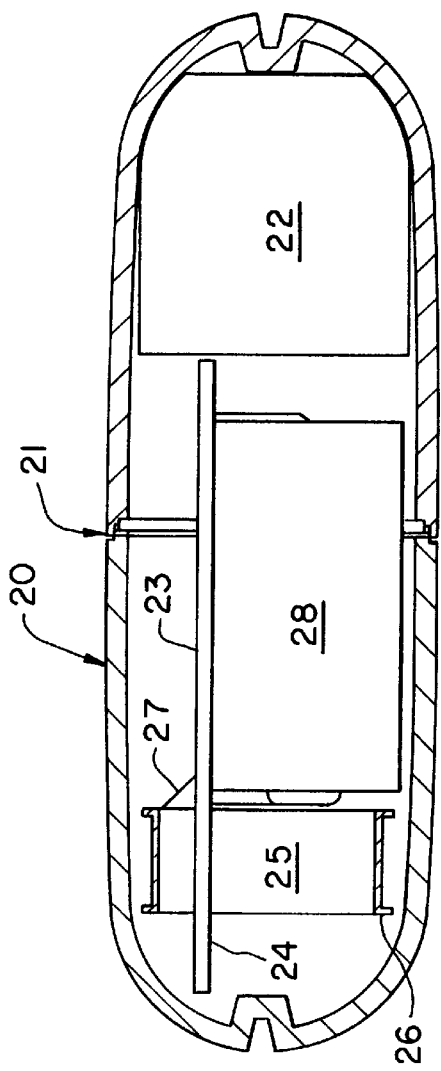
FIG. 5 is a longitudinal cross sectional view of an ingestible sensor which shows the non-electric structures.

FIG. 5 is a longitudinal cross sectional view of an ingestible bolus according to one embodiment of the present invention. The bolus includes a two-piece housing 20 which has a cylindrical shape with generally rounded or spherical shaped ends as depicted. The housing 20 is made from a material which will withstand the harsh environment within an animal's stomach and which will not adversely affect the animal. Plastics, including polyphenylene oxide (PPO) and ABS plastics, have been found to be particularly suitable for purposes of the present invention. As depicted, the two pieces or halves of the housing 20 are joined together at seam 21 which can be approximately midway along the bolus. The two pieces or halves of the housing 20 can be welded, glued or cemented together once all the internal components are assembled and positioned within the housing 20. FIG. 5 depicts the half portions of housing 20 as being attached together near the center of the ingestible bolus. In other embodiments, one of the housing portions could merely comprise an end cap for the overall cylindrical housing. The use of a cylindrical housing is believed to make the sensor easier to swallow for an animal and easier to manufacture. However, the sensor housing may have a cross sectional shape that is elliptical, polygonal, or flattened with curved sides.

A ballast or weight 22 is positioned within one end of housing 20. The weight 22 preferably has a solid cylindrical shape and an outer surface which is complimentary to the inner surface of the housing end in which it is inserted. If desired, the weight 22 can be fixed to the inside of the housing end by glue, cement, or other chemical or mechanical means. The weight 22 can be made of any material which is heavy enough to provide the ingestible sensor with an effective density of 1.75–2.0 $g/cm^3$ or greater. Ferric metals have the advantage of being attracted to any magnet present in an animal's rumen or reticulum. Such attraction can be advantageous if the antenna of the ingestible sensor is located at an opposite end of the housing. In such an arrangement, the end of the ingestible sensor in which the weight is located will be drawn to the magnet, causing the antenna to be positioned away from the magnet. This arrangement will help prevent the magnet from interfering with the data transmission from the antenna.

Weight 22 may also be made out of other types of metals such as brass, copper, lead, etc. to which magnets are not attracted. The advantage of such materials is that they will prevent the ingestible bolus from being in contact with any magnets present in an animal's rumen or reticulum. In further embodiments, weight 22 can be made from a magnetic or magnetizable material and used to attract and contain metal objects in the animal's rumen or reticulum.

A circuit board 23 which supports all the circuit elements is provided with a narrowed end portion 24 which is sized to pass through coil antenna 25 until the main portion of the circuit board 23 abuts the antenna coil 25. The antenna coil 25 includes a bobbin 26 which supports the antenna windings. The lead 27 from the antenna 25 to the circuit board 23 is depicted in FIG. 5.

The circuit board 22 is held in position within housing 20 by being wedged between the inner surface of the housing 20, coil antenna 25 and battery 28 which is attached to the circuit board 23. The battery 28 is preferably a long life battery such as a lithium battery which can operate the bolus under normal conditions for three years or more.

Figure 6:
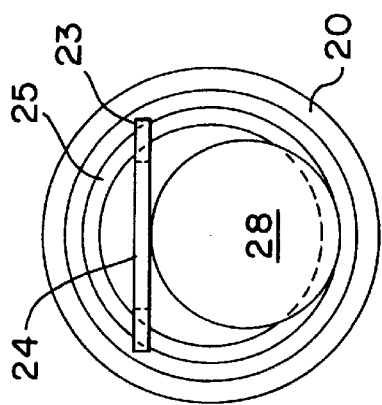
FIG. 6 is a radial cross sectional view of the ingestible sensor of FIG. 5.

FIG. 6 is a radial cross sectional view of the ingestible sensor of FIG. 5. The coil antenna 25 is depicted as being centered with housing 20 with the narrow portion 24 of the circuit board 23 positioned within coil antenna 25. In FIG. 6 the wider main portion of the circuit board 23 is depicted as abutting the coil antenna 25. The battery 28 is depicted in FIG. 6 as extending between the lower end of the circuit board 23 and the inner surface of the housing 20.

Figure 7:
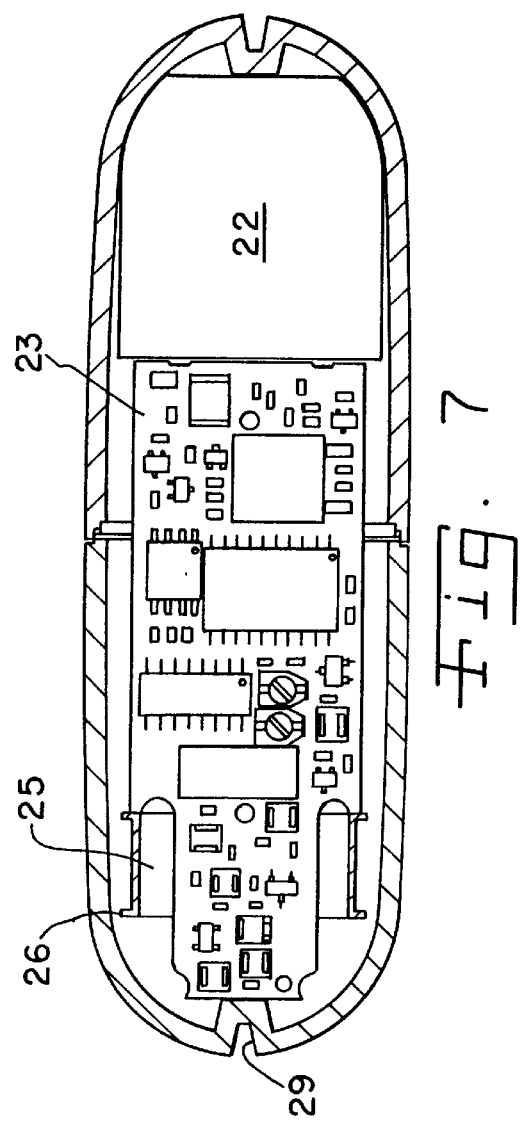
FIG. 7 is a longitudinal cross sectional view of an ingestible sensor which shows the relative positions of the electrical circuit elements.

FIG. 7 is a longitudinal cross sectional view of the ingestible bolus of FIG. 5 taken parallel to the top surface of the circuit board which depicts possible positions of the electrical circuit elements. As depicted in FIG. 7, by passing the circuit board 23 though the coil antenna 25, additional space is provided for attaching electrical components to the circuit board 23. It is noted that the inductor L4 which allows for external programming of the bolus is preferably located at the end of the circuit board 23 which is near weight 22. When inductor L4 is located in this position the weight 22 can augment inductor L4's magnetic pick up characteristics, particularly when weight 22 includes a magnetic material. An indentation 29 is provided at the end of the housing 20. The indentation 29 is provided for an alignment reference for automatic manufacturing and testing of the bolus.

Figure 8A:
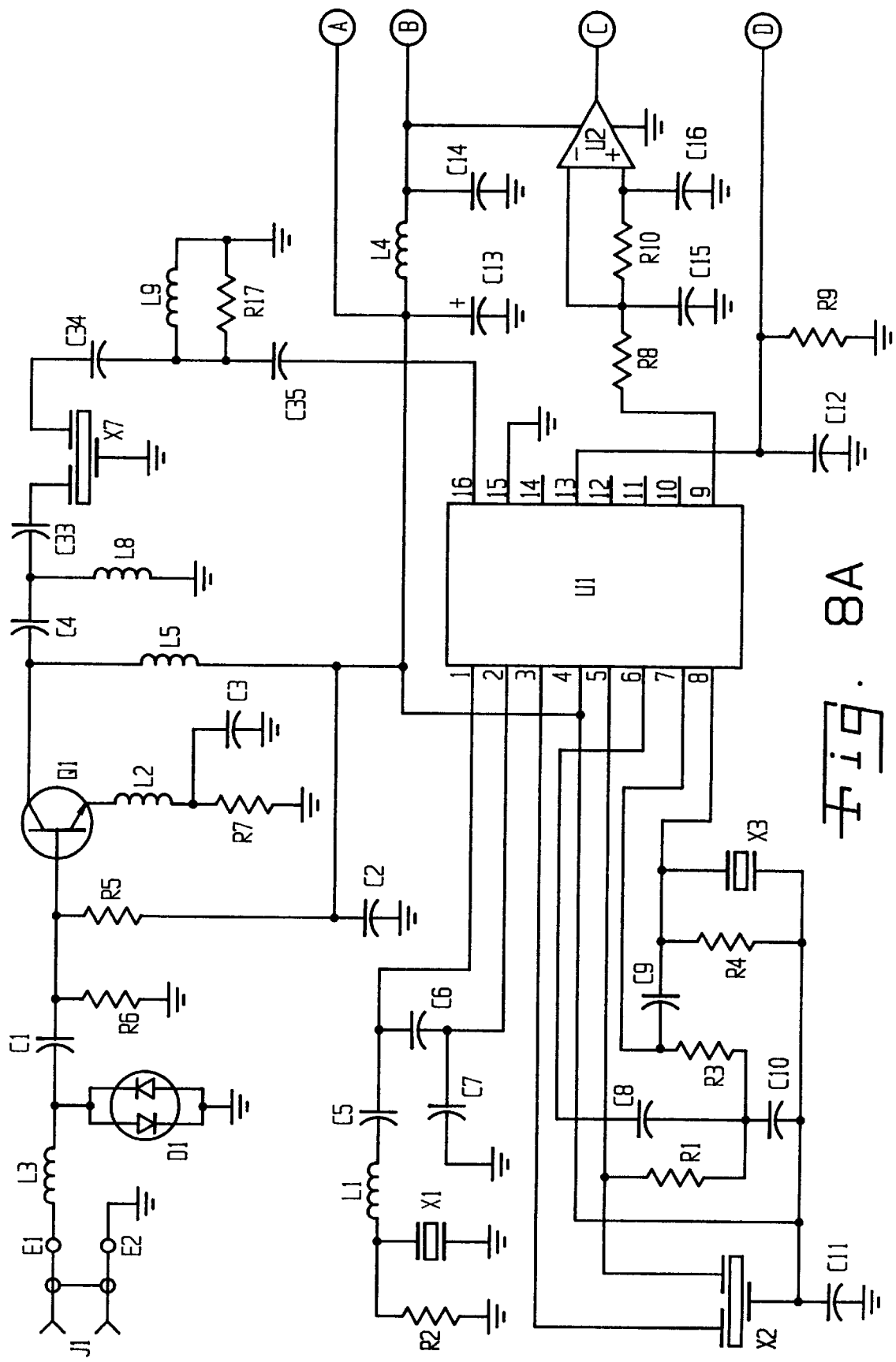
FIGS. 8A, 8B and 8C are a circuit diagram for a receiver/display according to one embodiment of the present invention which can be used in conjunction with the ingestible sensor.
Figure 8B:
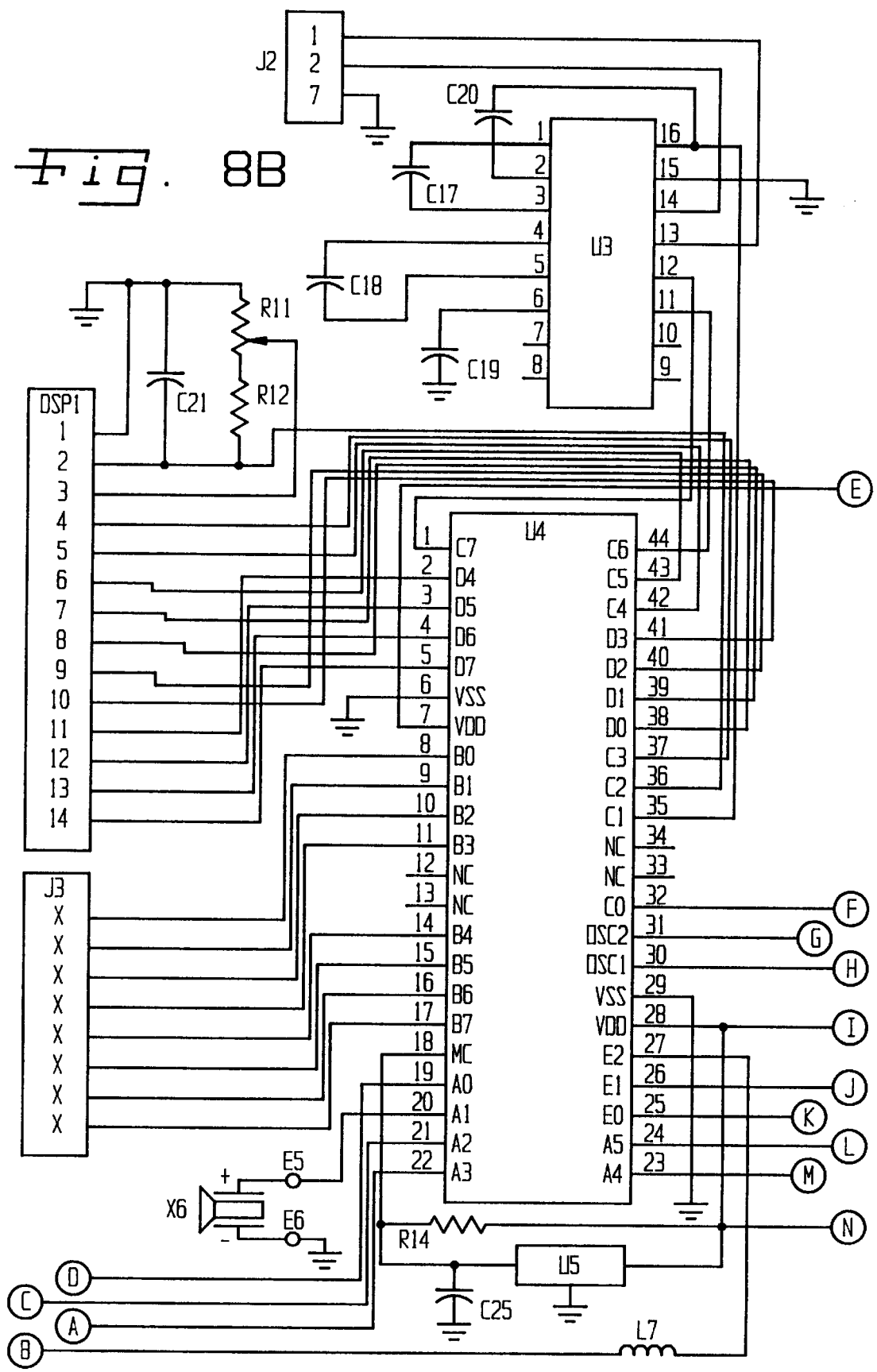
Figure 8C:
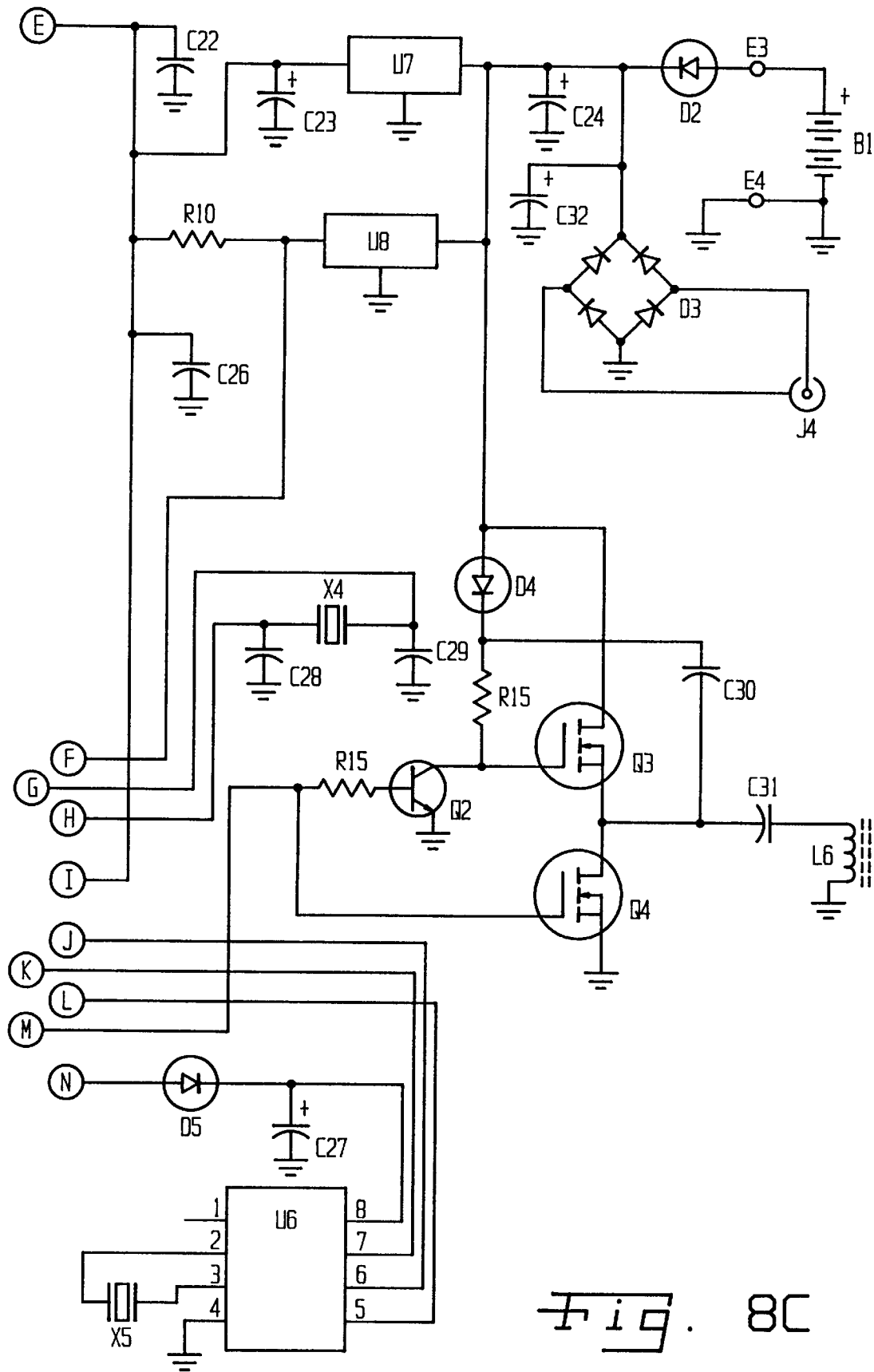

FIG. 8 (conjunctively 8A, 8B and 8C) is a circuit diagram for a receiver/display according to one embodiment of the present invention which can be used in conjunction with the ingestible sensor. This circuit could be used in either the portable hand held receiver 6 depicted in FIG. 1 or the non-portable receiver 4. The circuit depicted in FIGS. 8a and 8b includes a transistor amplifier circuit Q1 which causes preamplification of the input signal. Inductor L3 provides a matching element and diode D1 provides ESD protection. Resistors R5 and R6 serve as base bias resistors, C1 and C4 are input and output blocking capacitors respectively, DC bias filtering is provided by inductor L5 and capacitors C13 and C2, and emitter biasing is provided by inductor L2, resistor R7 and capacitor C3.

A two pole crystal filter X7 is used to filter image frequency and out-of-band noise and interference. The crystal X7 is preferably centered at 27.145 MHZ and has a 30 KHz 3 dB bandwidth and a 70 Khz 15 dB bandwidth. Inductor L8 and capacitor C33 form an input matching network. An output matching network is formed from capacitor C34, inductor L9 and resistor R17.

In FIG. 8a, U1 is a low power FM receiver chip. Pins 1 and 2 of this receiver chip are used to provide an on board Colpitis oscillator whose resonant frequency is determined by components C5, C6, C7, L1, X1, and R2. This 26.690 MHZ oscillator provides the local oscillator for down converting 27.145 MHZ to 455 Khz. The RF input at pin 16 is DC blocked by capacitor C35 and is mixed with the LO and a 455 Khz signal plus mixing products is output to pin 3. A ceramic four pole filter 455 Khz filter is used to filter the IF signal and feedback into the receiver chip's limiting amplifier pin 5 input. R1, C8, C10, P3 and C9 provide proper biasing for the limiting amplifier section. Crystal X3 and resistor P4 form the tank circuit for the FM demodulator. Pin 9 provides the amplifier demodulation baseband signal which is fed into a comparator circuit to square the data and provide a TTL/CMOS compatible signal to the microprocessor. The comparator circuit utilizes U2 as the comparator and R8 as an input resistor. C15, R10 and C16 provide a lowpass filter which controls the zero crossings of the comparator.

Pin 12 is the output signal of the logarithmic Received Signal Indicator (RSSI) which provides a voltage level output that is proportional to signal level and has a 90 dB dynamic range. This signal is lowpass filtered by resistor R9 and capacitor C12, and fed into the microprocessor's A/D convertor.

The receiver can be powered by a 9 volt battery or from an external 12 volt AC or DC power supply. Bridge rectifier D3 provides necessary rectification if an external AC supply is used. Capacitors C32 and C24 provide filtering of the rectified signal. If an external DC supply is used, the bridge rectifier provides two diode drops in DC input voltage and the filter capacitors are used. Diode D2 blocks current flow into the battery when using external power. U7 is a DC regulator that regulates the input voltage on pin 2 to +5 volts at pin 3 output. U8 is a low voltage detection circuit that pulls the output on pin 1 low when the input voltage on pin 2 falls below 6 volts. The microprocessor monitors this pin to insure proper voltages are present, and is designed to issue a "Low Battery" indication on the LED display if the voltage falls below 6 volts. U5 is a low voltage detector which is set at 2 volts and monitors the supply voltage to the microprocessor. This signal is monitored and can provide a shutdown of the microprocessor if the voltage falls below two volts.

U3 is an RS-232 transceiver chip that provides the correct voltages and signal protocol for RS-232 operation. Pin 14 is the receiver output to a host computer, and pin 13 is the input into the receiver from a host computer. Pin 11 is the CMOS data from the microprocessor for the transmission, and pin 1 is the CMOS output from the RS-232 transceiver chip received host computer data to the microprocessor. C17, C18, C19 and C20 are bypass capacitors for the transceiver chip.

U6 is a programmable timer chip that provides year, month, day and time information. The timer chip utilizes crystal X5 as its timing oscillator and has an on chip battery so that once it is set, it keeps time regardless of whether the power supply to the main circuit is on. The timer chip U6 is used to set the receiver time tag for data if a host PC is not present. The time is set by commands from the microprocessor in response to keypad commands or RS-232 commands. Pin 1 is reset, pin 6 is serial I/O line, and pin 7 is data clock for data transfer into and out of the timer chip.

MicroChip PIC16C74 microprocessor controls all timing, RS-232 communications, responds to keypad entries, issues all commands to LED display, switches power ON/OFF to RS-232 circuit, and receiver circuit for low power RCVR Off condition. The microprocessor also controls data to program the ingestible bolus via a 10 KHz transmitter circuit.

The microprocessor provides a 10 KHz modulated signal to resistor R15 and gate of FET Q4. The FET's Q3 and Q4 form a bootstrapped push pull arrangement. Diode D4, resistor R16 and capacitor C30 are used to bootstrap the gate of Q3 so that it can be an NMOS enhancement FET like Q4 instead of using a complementary PMOS FET as is normally seen in a push pull configuration. Q2 is used to invert the signal to the gate of Q3. Capacitor C31 and inductor L6 form a resonant circuit at 10 KHz and inductor L6 radiates a 10 KHz modulated signal that can be received by a bolus for external programming of the bolus. The coil is placed at the inner edge of the receiver case so that bolus can be placed on the outside of the receiver case for programming. According to another embodiment an external antenna can be used to increase the range at which the bolus can be programmed. The use of an antenna will allow programming of a bolus that is inside an animal.

FIG. 9 is a front view of a hand held receiver according to one embodiment of the present invention. FIG. 10 is a side view of the hand held receiver of FIG. 9. FIG. 11 is a top end view of the receiver of FIG. 9. As seen collectively in FIGS. 9–11, the receiver 6 includes a keypad 30 for inputting data and programming a bolus and a LED display 31 for displaying information such as mode settings, data input, transmitted and received data, etc. An RF connection 32 is provided to connect an antenna to the receiver. A battery charge jack 33 is provided to recharge the battery and/or supply external power to the receiver. A multi-pin connector 34 is provided to line the receiver to a PC or other processor for data transfer.

Referring now to FIG. 12, another embodiment of an ingestible bolus 50 of the present invention is shown. Bolus 50 generally includes a housing 52 and a plurality of electrical components 54 disposed within housing 52.

Housing 52 includes two housing halves 56 and 58, with each housing half 56 and 58 being formed from a material which is substantially biologically inert. For example, housing halves 56 and/or 58 may be formed from a suitable plastic such as polyphenylene oxide (PPO) or acrylonitrile butadiene styrene (ABS), or other suitable plastic. Alternatively, housing halves 56 and/or 58 may be formed from a suitable metal such as stainless steel, cobalt-chromium-molybdenum, titanium, etc. In the embodiment shown, housing half 56 is formed from 416 stainless steel and housing half 58 is formed from ABS plastic. Stainless steel housing half 56 is magnetic and thus may be attracted to a hardware magnet within the stomach of a ruminant animal. Other types of ferric metals which are magnetic and/or magnetizable and also substantially biologically inert may also be used (e.g., a suitable carbon steel with an appropriate plating or coating).

Metal housing half 56 has a weight which is sufficient to maintain bolus 50 within the stomach of the ruminant animal. More particularly, bolus 50 has an effective density of at least 1.75 g/cm$^3$; more preferably has an effective density of between 1.75 and 3.0 g/cm$^3$; and even more preferably has an effective density of approximately 2.7 g/cm$^3$. In the embodiment shown, bolus 50 has an overall volume of 43.34 cm$^3$. When housing 52 is empty without electronic components 54 being disposed therein, housing 52 has a weight of approximately 75.1 grams. On the other hand, with electric components 54 disposed within housing 52, bolus 50 has a weight of approximately 116 grams. Thus, the overall effective density of bolus 50 with electric components 54 disposed therein is approximately 2.68 g/cm$^3$. The effective density of bolus 50 is thus more than enough to maintain bolus 50 within the stomach of the ruminant animal.

Plastic housing half 58 allows radio frequency (RF) signals which are emitted from electrical components 54 to be transmitted to a remote receiver unit.

Metal housing half 56 and plastic housing half 58 are configured to be snap-locked together in a substantially fluid-tight manner, thereby protecting electrical components 54 disposed within bolus 50 from biological fluids within the stomach of the ruminant animal. More particularly, metal housing half 56 and plastic housing half 58 each include an open end (not numbered) with respective beveled edges 60 and 62 adjacent thereto. Beveled edges 60 provide the dual functionality of allowing plastic housing half 58 to be radially inwardly deflected and snapped together with metal housing half 56, as well as defining a pair of crush seal grooves 64 and 66 which substantially deform O-ring seals 68 to form a redundant sealing arrangement at the interface between housing halves 56 and 58. More specifically, when the open ends of housing halves 56 and 58 are placed against each other to be snap-locked together and further moved towards each other in an axially compressive manner, both an axial as well as a radially inward compressive force is applied to plastic housing half 58. The radially inward force exerted on beveled edge 62 by beveled edge 64 radially inwardly deflects the open end of plastic housing half 58 to allow plastic housing half 58 to be further axially slid to the position shown in FIG. 12. When snap-locked together, metal housing half 56 and plastic housing half 58 define the two crush seal grooves 64 and 66 therebetween for receiving respective O-ring seals 68. The cross-sectional area of seal grooves 64 and 66 is substantially the same as the cross-sectional area of the O-ring seals 68 when in a non-deflected state. Thus, when metal housing half 56 and plastic housing half 58 are snap-locked together, O-ring seal 68 is deformed to substantially fill the cross-sectional areas of seal grooves 64 and 66. This crush seal arrangement prevents slippage or movement of O-ring seal 68 within seal grooves 64 and 66, and thus provides a very effective fluid seal regardless of slight relative movements between housing halves 56 and 58 caused by external forces, thermal expansions and contractions, etc.

Electrical components 54 generally include a power source or battery 70, a printed circuit board 72 carrying a plurality of electrical components such as a temperature sensor 73 and other components defining a transmitter circuit 74 (shown schematically in FIG. 12) for transmitting an air-borne data burst to a remote receiver unit, and an antenna 76 electrically connected with transmitter 74 through appropriate electrical connections in printed circuit board 72.

Battery 70 provides a suitable voltage to electrical components carried by printed circuit board 72. In the embodiment shown, battery 70 is a three-volt alkaline battery providing an adequate life to bolus 50. Battery 70 is disposed radially within a compression coil spring 78, and axially engages a coil spring 80 and a resilient disc 84. Coil spring 78 engages metal housing half 56 at one end thereof, and engages a shoulder 84 on printed circuit board 72 at another end thereof. Coil spring 80 engages one pole of battery 70 at one end thereof, and engages a pair of notches 86 in printed circuit board 72 at the opposite end thereof. The end of coil spring 80 within notches 86 is electrically connected with electrical components on printed circuit board 72. Coil springs 78 and 80 and resilient disc 82 ensure that battery 70 is properly electrically connected with electrical components carried on printed circuit board 72, regardless of vibrations, etc.

Antenna 76 is helically wrapped around an end of printed circuit board 72 for purposes of convenient manufacturing.

Antenna 76 is at least partially disposed within plastic housing half 58 so that signals emitted from antenna 76 may be effectively transmitted to the ambient environment outside of bolus 50. Preferably, antenna 76 is entirely disposed within plastic housing half 58 and not within metal housing half 56.

In the embodiment shown, seal grooves 64 and 66 each have a substantially triangular cross section, and elastomeric O-ring seals 68 have a substantially circular cross section. However, it is also possible that seal grooves and O-rings with different cross-sectional shapes may be utilized. Regardless of the particular cross-sectional shape used, the elastomeric seal should substantially fill the cross-sectional area defined by the seal grooves.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

What is claimed is:

1. An ingestible bolus for ingestion in a stomach of a ruminant animal, comprising:
    a housing including two housing halves, each of said halves comprised of a biologically inert material, each of said housing halves consisting essentially of plastic;
    a plurality of electrical components disposed within said housing, said electrical components including a power source, an air-borne signal transmitter for transmitting a data burst, and an antenna connected with said transmitter, said antenna disposed entirely within one said plastic housing half; and
    means for ballasting said housing with a weight sufficient to maintain said bolus within the stomach of the ruminant animal, said ballasting means being disposed entirely within an other said plastic housing half, said ballasting means including a ferric metal material.

2. The ingestible bolus of claim 1, wherein said ballasting means provides said bolus with an effective density of at least 1.75 grams per cubic centimeter.

3. The ingestible bolus of claim 2, wherein said ballasting means provides said bolus with an effective density of between 1.75 and 2.0 grams per cubic centimeter.

4. The ingestible bolus of claim 1, wherein said plastic consists essentially of one of polyphenylene oxide and acrylonitrile butadiene styrene.

5. The ingestible bolus of claim 1, wherein said ballasting means comprises a ballast weight disposed within said housing.

6. The ingestible bolus of claim 1, wherein said antenna is disposed entirely within said plastic housing half and said ballasting means is associated with the other said housing half.

7. The ingestible bolus of claim 1, wherein one of said housing halves consists essentially of a plastic and an other of said housing halves consists essentially of a metal.

8. The ingestible bolus of claim 7, wherein said metal defines said ballasting means.

9. The ingestible bolus of claim 7, wherein each of said housing halves include an open end, said open ends being configured to snap-lock together in a substantially fluid-tight manner.

10. The ingestible bolus of claim 9, wherein one of said housing halves defines at least one annular groove at an inside diameter of a corresponding said open end, and an other of said housing halves defines at least one mating annular groove at an outside diameter of a corresponding said open end, and further comprising at least one fluid seal, each said fluid seal disposed in a corresponding mating pair of said annular grooves.

11. The ingestible bolus of claim 10, wherein each said fluid seal comprises an elastomeric O-ring.

12. The ingestible bolus of claim 11, wherein each said mating pair of annular grooves conjunctively define a crush seal groove with a substantially triangular cross-section, each said O-ring substantially filling said corresponding crush seal groove.

13. The ingestible bolus of claim 10, wherein said one housing half includes two annular grooves, said other housing half includes two mating annular grooves, and said at least one fluid seal comprises two fluid seals, each said fluid seal disposed in a corresponding mating pair of said annular grooves.

14. An ingestible bolus for ingestion in a stomach of a ruminant animal, comprising:
    a housing including two housing halves, each of said halves comprised of a biologically inert material, one of said housing halves consisting essentially of plastic, an other of said housing halves consisting essentially of metal;
    a plurality of electrical components disposed within said housing, said electrical components including a power source, an air-borne signal transmitter for transmitting a data burst, and an antenna connected with said transmitter, said antenna disposed at least partially within said at least one plastic housing half; and
    means for ballasting said housing with a weight sufficient to maintain said bolus within the stomach of the ruminant animal.

15. The ingestible bolus of claim 14, wherein said metal consists essentially of stainless steel.

16. The ingestible bolus of claim 15, wherein said stainless steel is one of magnetic and magnetizable.

17. The ingestible bolus of claim 15, wherein said stainless steel consists essentially of 416 stainless steel.

18. An ingestible bolus for ingestion in a stomach of a ruminant animal, comprising:
    a housing including two housing halves, each of said halves comprised of a biologically inert material, at least one of said housing halves consisting essentially of plastic, each of said housing halves including an open end, one of said housing halves having an inside distal projection and at least one inside annular groove at an inside diameter of a corresponding said open end, an other of said housing halves having an outside distal projection and at least one outside annular groove at an outside diameter of a corresponding said open end, said inside distal projection being snap locked into said at least one outside annular groove, said outside distal projection being snap locked into said at least one inside annular groove;
    a plurality of electrical components disposed within said housing, said electrical components including a power source, an air-borne signal transmitter for transmitting a data burst, and an antenna connected with said transmitter, said antenna disposed at least partially within said at least one plastic housing half; and
    means for ballasting said housing with a weight sufficient to maintain said bolus within the stomach of the ruminant animal.

19. The ingestible bolus of claim 18, wherein each said groove is defined by a monolithic portion of said respective housing half.

* * * * *

UNITED STATES PATENT AND TRADEMARK OFFICE
CERTIFICATE OF CORRECTION

PATENT NO. : 6,099,482
DATED : August 8, 2000
INVENTOR(S) : Scott A. Brune, et al.

It is certified that error appears in the above-identified patent and that said Letters Patent is hereby corrected as shown below:

COLUMN 10

Line 8, delete "P3" and substitute --R3-- therefor; and

Line 10, delete "P4" and substitute --R4-- therefor.

Signed and Sealed this

Seventeenth Day of April, 2001

Attest:

NICHOLAS P. GODICI

Attesting Officer        Acting Director of the United States Patent and Trademark Office